US012746319B2

(12) United States Patent
Planas et al.

(10) Patent No.: US 12,746,319 B2
(45) Date of Patent: Sep. 29, 2026

(54) SYSTEMS AND METHODS FOR IMPLEMENTING DIFFERENT VERSIONS OF A BLOOD SEPARATION PROCEDURE

(71) Applicant: Fenwal, Inc., Lake Zurich, IL (US)

(72) Inventors: Samantha M. Planas, Wauconda, IL (US); Kyungyoon Min, Kildeer, IL (US); Amit J. Patel, Algonquin, IL (US); Thomas Gniadek, Deerfield, IL (US)

(73) Assignee: Fenwal, Inc., Lake Zurich, IL (US)

(*) Notice: Subject to any disclaimer, the term of this patent is extended or adjusted under 35 U.S.C. 154(b) by 543 days.

(21) Appl. No.: 18/130,503

(22) Filed: Apr. 4, 2023

(65) Prior Publication Data

US 2023/0321334 A1 Oct. 12, 2023

Related U.S. Application Data

(60) Provisional application No. 63/348,839, filed on Jun. 3, 2022, provisional application No. 63/327,869, filed on Apr. 6, 2022.

(51) Int. Cl.
*A61M 1/36* (2006.01)
*B01D 63/16* (2006.01)

(52) U.S. Cl.
CPC ........... *A61M 1/3693* (2013.01); *B01D 63/16* (2013.01); *A61M 2205/3379* (2013.01); *A61M 2205/505* (2013.01); *B01D 2201/54* (2013.01); *B01D 2313/701* (2022.08)

(58) Field of Classification Search
CPC ................ A61M 1/3693; A61M 1/385; A61M 2205/3379; A61M 2205/505; B01D 63/16; B01D 2201/54; B01D 2313/701
See application file for complete search history.

(56) References Cited

U.S. PATENT DOCUMENTS

| | | | | |
|---|---|---|---|---|
| 5,194,145 | A | 3/1993 | Schoendorfer | |
| 5,234,608 | A | 8/1993 | Duff | |
| 2002/0033370 | A1 * | 3/2002 | Bainbridge | A61M 1/303 604/6.11 |
| 2004/0199098 | A1 * | 10/2004 | Pierce | A61M 1/3603 604/4.01 |
| 2006/0052949 | A1 * | 3/2006 | Fletcher-Haynes | G16H 10/60 702/21 |
| 2017/0296718 | A1 * | 10/2017 | Kimura | B04B 11/02 |

FOREIGN PATENT DOCUMENTS

| | | |
|---|---|---|
| WO | 2012125457 | 9/2012 |

OTHER PUBLICATIONS

Extended European Search Report for European Patent Application No. 23166497.0-1113, dated Jun. 29, 2023.
"Persona | Plasma Collection Solution" brochure, Haemonetics Corporation, 2020, 4 pages.

* cited by examiner

*Primary Examiner* — Liam Royce
(74) *Attorney, Agent, or Firm* — Cook Alex Ltd.

(57) ABSTRACT

A blood separation device has a controller configured to execute a first and a second version of a blood separation procedure. Information regarding a blood source is analyzed to determine whether to implement the first version of the procedure or the second version. This may include an analysis of the age, weight, and/or sex of the blood source, along with whether the blood source has previously been the subject of a blood separation procedure. The second version may allow for a greater percentage of the blood or red blood cells of the blood source to be outside of the body of the blood source (in a fluid flow circuit mounted to the device) at any time during the procedure. The second version may also or alternatively allow for a higher blood cell separation efficiency than the first version, along with separating the blood in a larger blood separation chamber.

23 Claims, 8 Drawing Sheets

SYSTEMS AND METHODS FOR IMPLEMENTING DIFFERENT VERSIONS OF A BLOOD SEPARATION PROCEDURE

CROSS-REFERENCE TO RELATED APPLICATIONS

This application claims the benefit of and priority of U.S. Provisional Patent Application Ser. No. 63/327,869, filed Apr. 6, 2022, and U.S. Provisional Patent Application Ser. No. 63/348,839, filed Jun. 3, 2022, the contents of each of which are incorporated by reference herein.

BACKGROUND

Field of the Disclosure

The present disclosure relates to blood separation systems and methods. More particularly, the present disclosure relates to systems and methods for implementing different versions of a blood separation procedure.

Description of Related Art

Various blood processing systems now make it possible to collect particular blood constituents, instead of whole blood, from a blood source such as, but not limited to, a container of previously collected blood or other living or non-living source. Blood is typically separated into its constituents (e.g., red cells, platelets, and plasma) through centrifugation, such as in the AMICUS® blood processing system from Fenwal, Inc. of Lake Zurich, Illinois, which is an affiliate of Fresenius Kabi AG of Bad Homburg, Germany, or other centrifugal separation devices, or a spinning membrane-type separator, such as the AUTOPHERESIS-C® and AURORA® blood processing systems from Fenwal, Inc. In such systems, whole blood is drawn from a blood source, the particular blood component or constituent is separated, removed, and collected, and the remaining blood constituents are returned to the blood source.

Removing only particular constituents is advantageous when the blood source is a human donor because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method is provided for implementing a blood separation procedure. The method includes selecting a first blood separation device configured to execute a first version of a blood separation procedure and a second blood separation device configured to execute a second version of the blood separation procedure or a single blood separation device configured to execute the first and second versions of the blood separation procedure. It is determined whether a blood source is qualified for the first version of the blood separation procedure or the second version of the blood separation procedure and/or whether a blood source is not qualified for the first version of the blood separation procedure or the second version of the blood separation procedure. The first version of the blood separation procedure is implemented for the blood source upon determining that the blood source is qualified for the first version of the blood separation procedure and/or upon determining that the blood source is not qualified for the second version of the blood separation procedure. The second version of the blood separation procedure is instead implemented for the blood source upon determining that the blood source is qualified for the second version of the blood separation procedure and/or upon determining that the blood source is not qualified for the first version of the blood separation procedure.

In another aspect, a blood separation device includes a pump system, a clamp system, a separation actuator, and a controller. The controller is programmed with first and second versions of a blood separation procedure in which the pump system, the clamp system, and the separation actuator are actuated to draw blood from a blood source, separate the blood into at least two blood components, and convey at least a portion of one of said blood components to a recipient. The controller is configured to determine or be instructed that the blood source is qualified for the first version of the blood separation procedure or the second version of the blood separation procedure and/or determine or be instructed that the blood source is not qualified for the first version of the blood separation procedure or the second version of the blood separation procedure. The controller implements the first version of the blood separation procedure for the blood source upon determining or being instructed that the blood source is qualified for the first version of the blood separation procedure and/or upon determining or being instructed that the blood source is not qualified for the second version of the blood separation procedure. The controller instead implements the second version of the blood separation procedure for the blood source upon determining or being instructed that the blood source is qualified for the second version of the blood separation procedure and/or upon determining or being instructed that the blood source is not qualified for the first version of the blood separation procedure.

In yet another aspect, a blood separation device includes a pump system, a clamp system, a separation actuator, and a controller. The controller is configured to actuate the pump system, the clamp system, and the separation actuator to execute a blood separation procedure in which a volume of blood having a volume of red blood cells is present in a fluid flow circuit. The controller is further configured to be instructed of a maximum percentage and/or maximum volume of a total blood volume of a blood source that may be present in the fluid flow circuit at any one time during said blood separation procedure and/or a maximum percentage and/or maximum volume of a pre-procedure red blood cell volume of the blood source that may be present in the fluid flow circuit at any one time during said blood separation procedure.

In another aspect, a computer-implemented method is provided for executing a blood separation procedure using a first blood separation device configured to execute a first version of a blood separation procedure and a second blood separation device configured to execute a second version of the blood separation procedure or a single blood separation device configured to execute the first and second versions of the blood separation procedure. The method includes determining whether a blood source is qualified for the first version of the blood separation procedure or the second version of the blood separation procedure and/or determining whether a blood source is not qualified for the first version of the blood separation procedure or the second version of the blood separation procedure. The first version of the blood separation procedure is initiated (or an operator is prompted to initiate the first version of the procedure) for the blood source upon determining that the blood source is qualified for the first version of the blood separation procedure and/or upon determining that the blood source is not qualified for the second version of the blood separation procedure. The second version of the blood separation procedure is initiated (or an operator is prompted to initiate the second version of the procedure) for the blood source upon determining that the blood source is qualified for the second version of the blood separation procedure and/or upon determining that the blood source is not qualified for the first version of the blood separation procedure.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
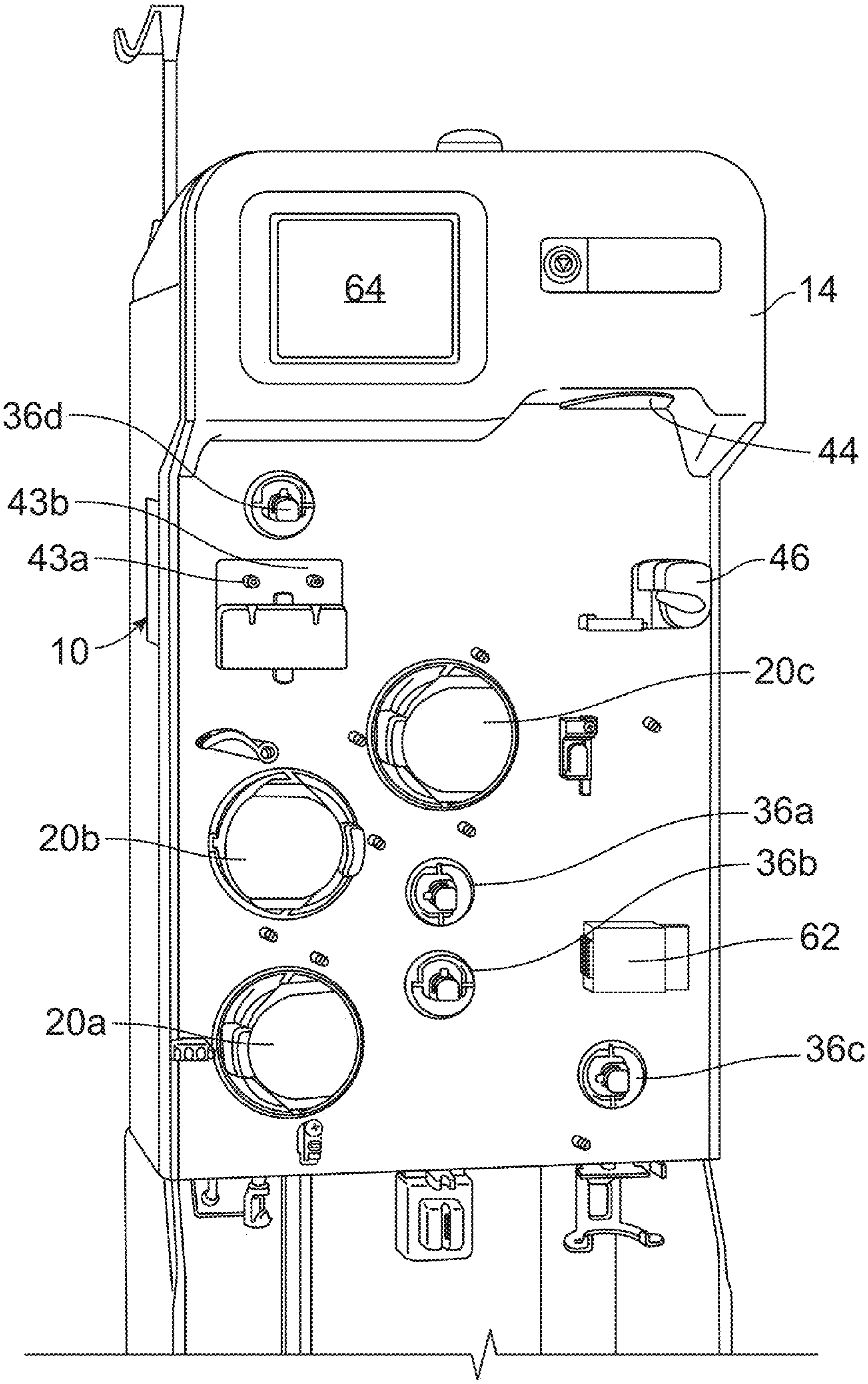
FIG. 1 is a front perspective view of an exemplary blood separation device according to an aspect of the present disclosure.
Figure 2:
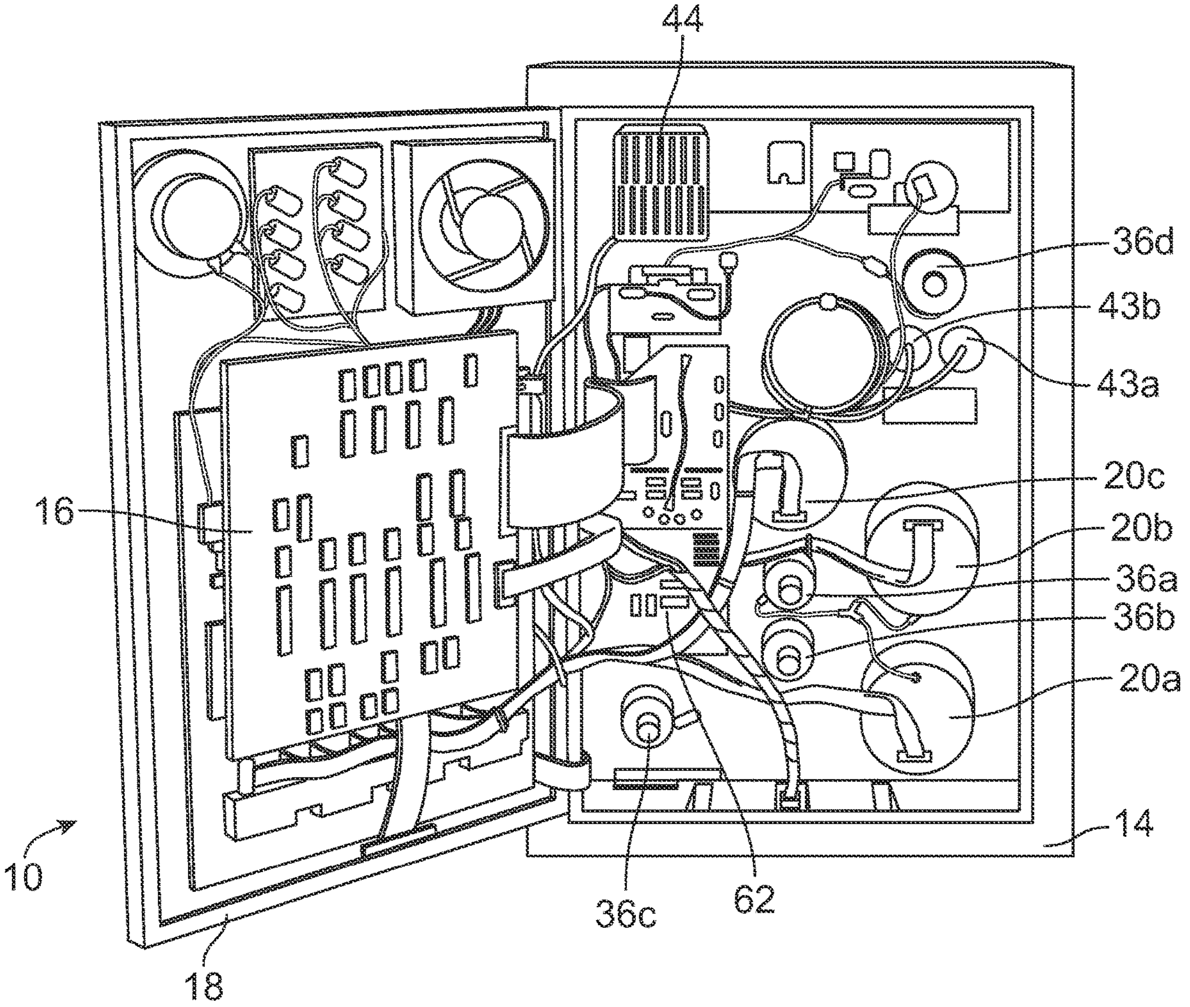
FIG. 2 is a rear perspective view of the blood separation device of FIG. 1, with a rear door thereof in an open position.
Figure 3:
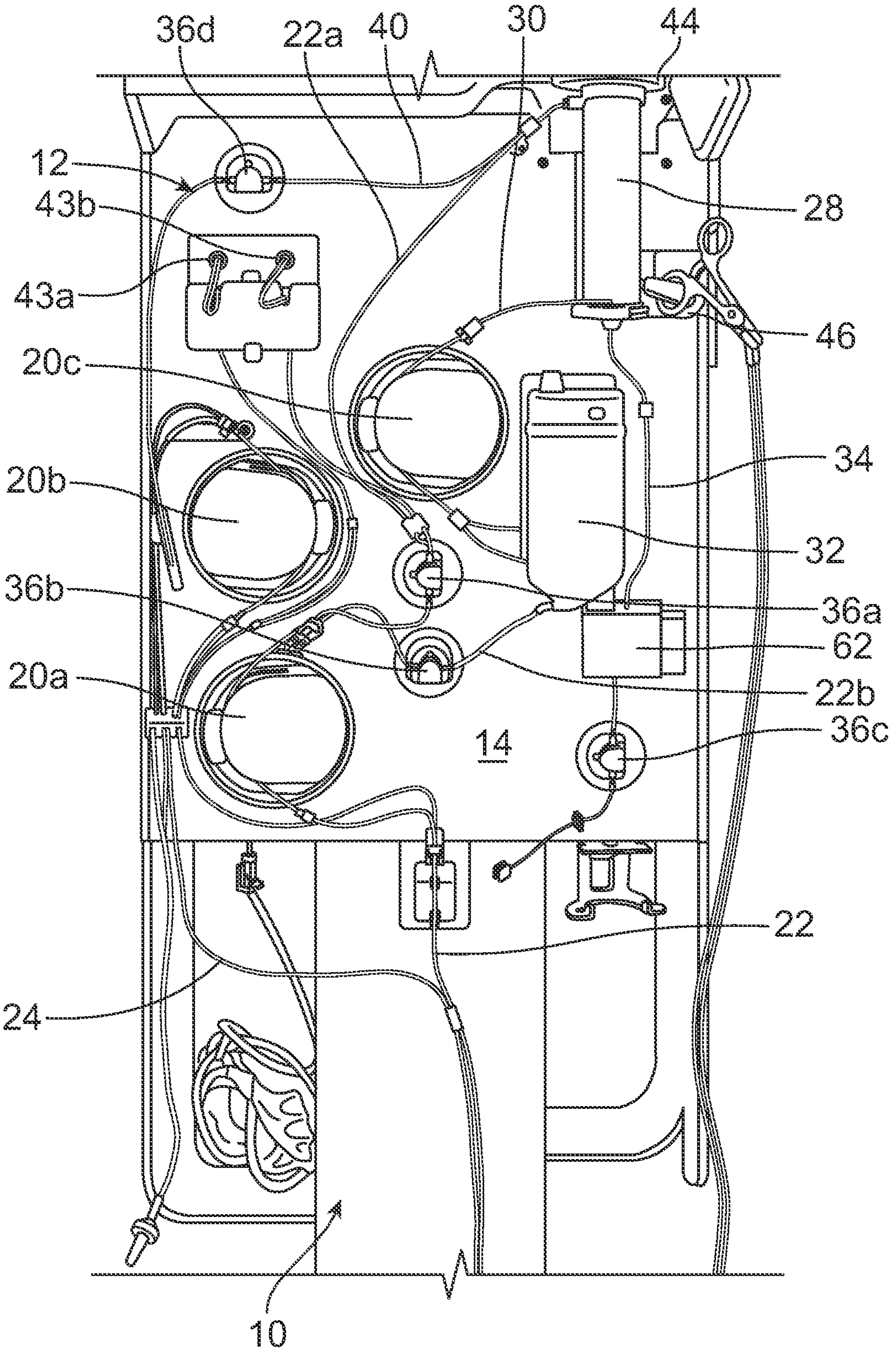
FIG. 3 is a front perspective view of the blood separation device of FIG. 1, with a fluid flow circuit associated therewith to constitute a blood separation system.

According to an aspect of the present disclosure, a durable or reusable blood separation device is used in combination with a separate fluid flow circuit (which may be disposable) to separate blood into two or more constituents. FIGS. 1 and 2 illustrate an exemplary blood separation device 10, while FIG. 3 illustrates an exemplary fluid flow circuit 12 mounted onto the blood separation device 10 (with the combination referred to herein as a "blood separation system"). It should be understood that the illustrated blood separation device 10 and fluid flow circuit 12 are merely exemplary of such devices and circuits and that differently configured blood separation devices and fluid flow circuits may be provided without departing from the scope of the present disclosure.

The device 10 of FIG. 1 is configured for processing whole blood, but it may be used to process any other plasma-containing fluid to separate plasma from concentrated fluid (which may be red cell concentrate or packed red cells when the plasma-containing fluid constitutes whole blood). The plasma-containing fluid may come from any fluid source, which may include a living donor or patient (e.g., a human blood donor) or a non-living source (e.g., a blood bag or fluid container).

The illustrated device 10 includes a cabinet or housing 14, with several components positioned outside of the cabinet 14 (e.g., associated with a front wall or surface or panel of the cabinet 14) and additional components (including a central processing unit or controller 16) and interconnects positioned inside of the cabinet 14, which may be accessed by opening a rear door 18 of the device 10, as shown in FIG. 2. It should be understood that the illustrated components and the location of the components is merely exemplary, and that additional or different components and different component arrangements may be incorporated into the device without departing from the scope of the present disclosure.

Figure 5:
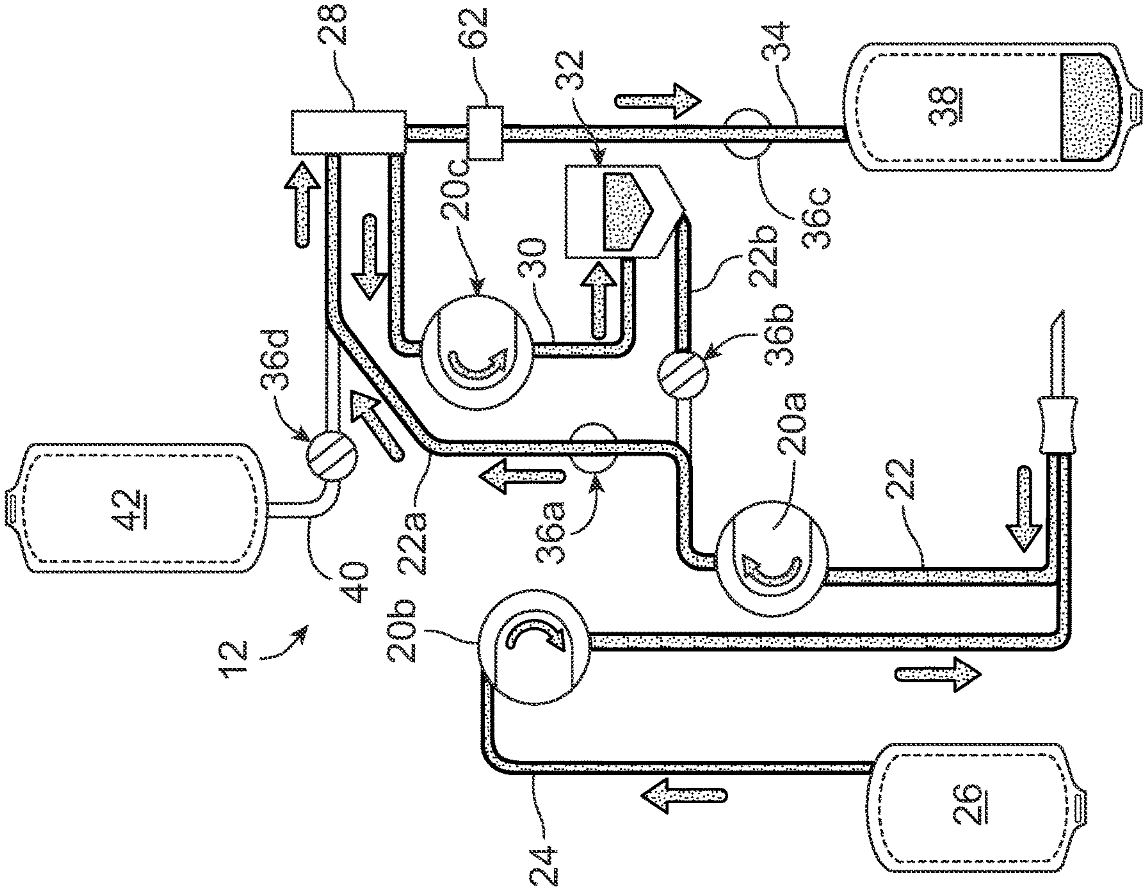
FIG. 5 is a schematic view of the blood separation system of FIG. 3, in a blood draw mode.
Figure 6:
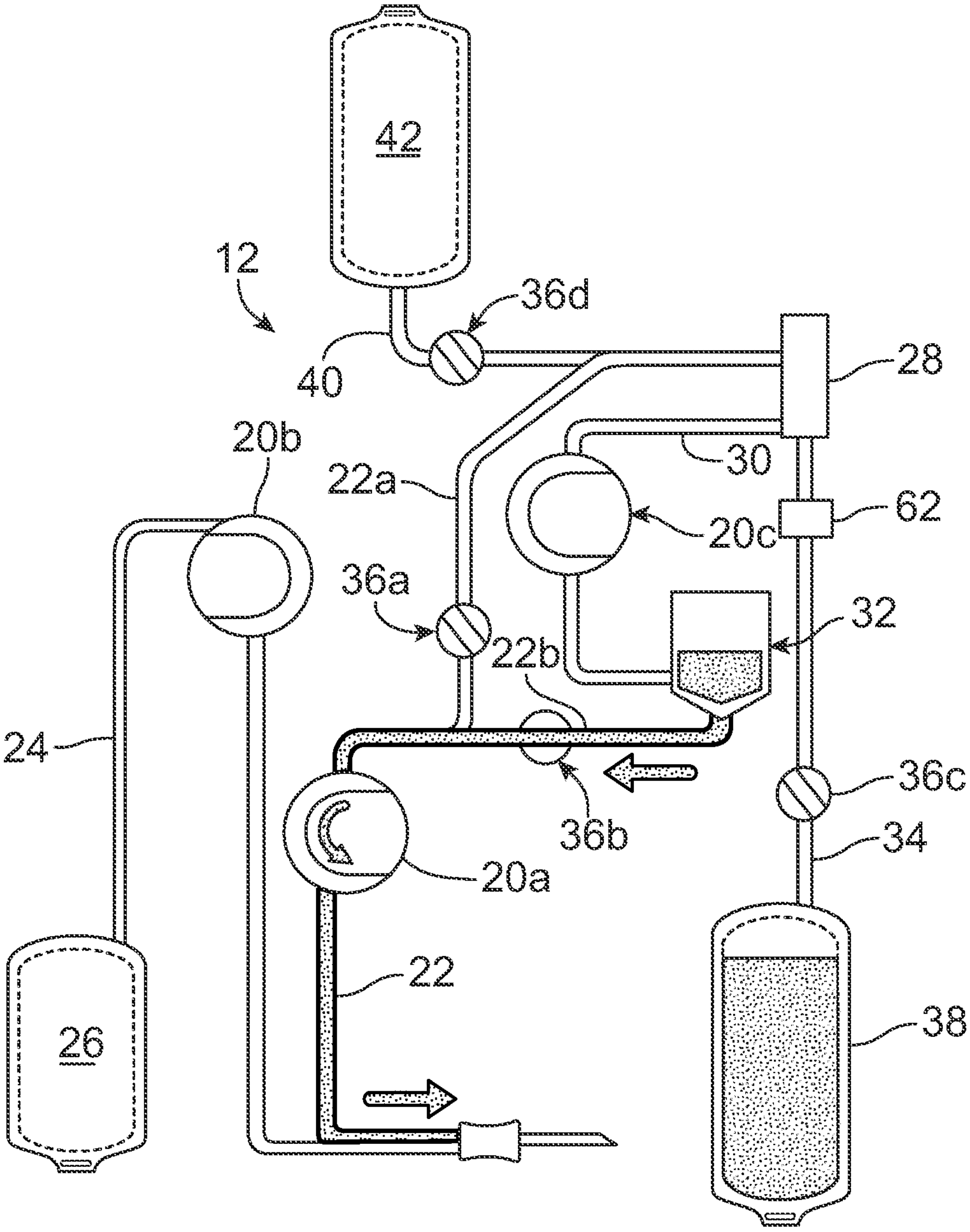
FIG. 6 is a schematic view of the blood separation system of FIG. 3, in a blood component return mode.
Figure 7:
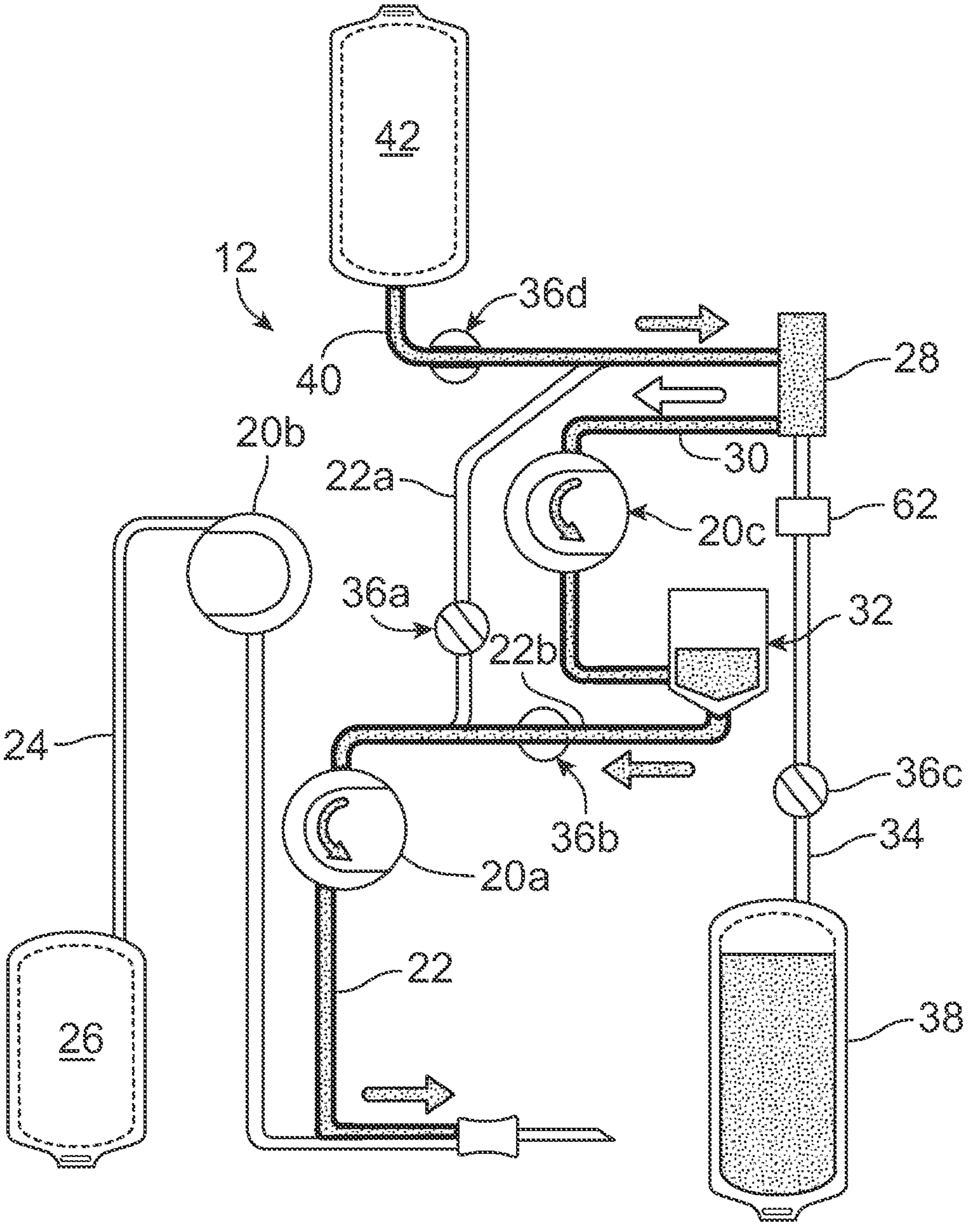
FIG. 7 is a schematic view of the fluid flow circuit and fluid processing system of FIG. 3, in a replacement fluid return mode.

Among the components positioned on the outside of the cabinet 14, one or more pumps or pump stations 20*a*-20*c* (collectively referred to herein as a "pump system") may be provided, with the pumps 20*a*-20*c* configured to accommodate tubing lines of the fluid flow circuit 12. One of the pumps 20*a* may be provided as a source/recipient access pump, which may be associated with a source/recipient access line 22 of the fluid flow circuit 12 and operates to draw fluid from a fluid source (FIG. 5) and to return fluid to a fluid recipient (FIGS. 6 and 7). Another one of the pumps 20*b* may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a blood separation module or chamber 28 of the fluid flow circuit 12. A third pump 20*c* may be provided as a concentrated fluid pump, which may be associated with a concentrated fluid outlet line 30 and operates to draw concentrated fluid from the blood separation chamber 28 and direct it into a concentrated fluid reservoir 32 after the fluid has been separated into a concentrated fluid and separated plasma in the blood separation chamber 28.

In the illustrated embodiment, the pumps 20*a*-20*c* are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a plasma outlet line 34 of the fluid flow circuit 12 to draw separated plasma from the blood separation chamber 28 after the plasma-containing fluid has been separated into a concentrated fluid and separated plasma. Also, as will be described in greater detail herein, the illustrated embodiment employs a single fluid flow tubing or flow path for both drawing blood from a source and flowing or returning fluids to a recipient, which are carried out intermittently. The system 10 could employ separate draw and return flow paths or tubes without departing from the scope of the present disclosure.

In addition to the pumps 20*a*-20*c*, the external components of the device 10 may include one or more clamps or valves 36*a*-36*d* (collectively referred to herein as a "clamp system") associated with the tubing lines of the fluid flow circuit 12. The clamps or valves 36*a*-36*d* may be variously configured and operate to selectively allow or prevent fluid flow through the associated tubing line. In the illustrated embodiment, one clamp or valve 36*a* may be provided as a fluid source/recipient clamp, which may be associated with a draw branch 22*a* of the source/recipient access line 22 of the fluid flow circuit 12 to allow (FIG. 5) or prevent (FIGS. 6 and 7) the flow of fluid through the draw branch 22*a* of the source/recipient access line 22. Another one of the clamps or valves 36*b* may be provided as a reinfusion clamp or valve, which may be associated with a reinfusion branch 22*b* of the source/recipient access line 22 downstream of a concentrated fluid reservoir 32 of the fluid flow circuit 12 to allow (FIGS. 6 and 7) or prevent (FIG. 5) the flow of concentrated fluid through the reinfusion branch 22*b*. A third clamp or valve 36*c* may be provided as a plasma clamp or valve, which may be associated with the plasma outlet line 34 to allow (FIG. 5) or prevent (FIGS. 6 and 7) the flow of separated plasma through the plasma outlet line 34 and into a separated plasma container 38. A fourth clamp or valve 36*d* may be provided as a replacement fluid clamp or valve, which may be associated with a replacement fluid line 40 of the fluid flow circuit 12 to allow (FIG. 7) or prevent (FIGS. 5 and 6) the flow of a replacement fluid out of a replacement fluid source 42 (e.g., a bag or container at least partially filled with saline). Additional or alternative clamps or valves may also be provided without departing from the scope of the present disclosure.

The illustrated device 10 further includes one or more pressure sensors 43*a* and 43*b* that may be associated with the fluid flow circuit 12 to monitor the pressure within one or more of the tubing lines of the fluid flow circuit 12 during operation of the pumps 20*a*-20*c* and clamps or valves 36*a*-36*d*. In one embodiment, one pressure sensor 43*a* may be associated with a tubing line that draws fluid from a fluid source and/or directs processed fluid to a fluid recipient, while the other pressure sensor 43*b* may be associated with a tubing line that directs fluid into or out of the blood separation chamber 28 to assess the pressure within the blood separation chamber 28, but the pressure sensors 43*a* and 43*b* may also be associated with other tubing lines without departing from the scope of the present disclosure. The pressure sensors 43*a* and 43*b* may send signals to the system controller 16 that are indicative of the pressure within the tubing line or lines being monitored by the pressure sensor 43*a*, 43*b*. If the controller 16 determines that an improper pressure is present within the fluid flow circuit 12 (e.g., a high pressure due to an occlusion of one of the tubing lines), then the controller 16 may instruct one or more of the pumps 20*a*-20*c* and/or one or more of the clamps or valves 36*a*-36*d* to act so as to alleviate the improper pressure condition (e.g., by reversing the direction of operation of one of the pumps 20*a*-20*c* and/or opening or closing one of the clamps or valves 36*a*-36*d*). Additional or alternative pressure sensors may also be provided without departing from the scope of the present disclosure.

Figure 4:
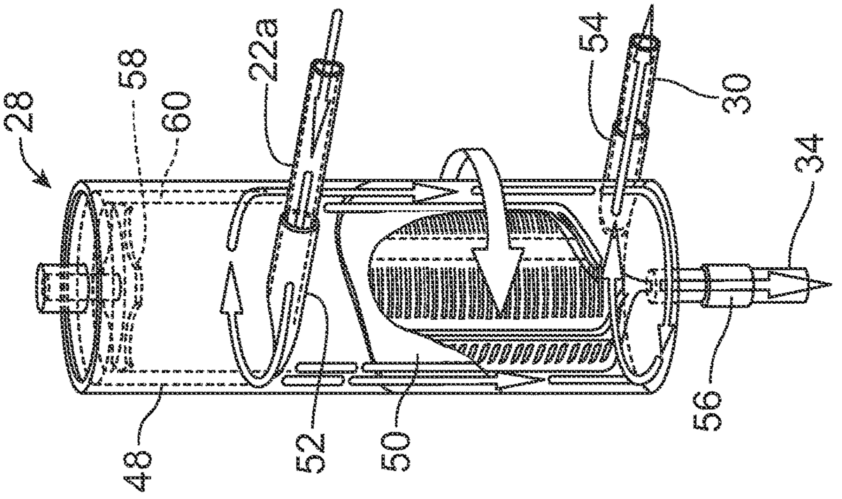
FIG. 4 is a front perspective view of a blood separation chamber of the fluid flow circuit of FIG. 3, with a portion thereof broken away for illustrative purposes.

The device 10 also includes a separation actuator 44 that interacts with a portion of the blood separation chamber 28 to operate the blood separation chamber 28. A chamber lock 46 may also be provided to hold the blood separation chamber 28 in place with respect to the cabinet 14 and in engagement with the separation actuator 44. The configuration and operation of the separation actuator 44 depends upon the configuration of the blood separation chamber 28. In the illustrated embodiment, the blood separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the blood separation chamber 28 may include a tubular housing 48 (FIG. 4), with a microporous membrane 50 positioned therein. An inlet 52 allows a fluid to enter into the housing 48 (via the draw branch 22*a* of the source/recipient access line 22), while a side outlet 54 allows concentrated fluid to exit the housing 48 (via the concentrated fluid outlet line 30) and a bottom outlet 56 allows separated plasma to exit the housing 48 (via the plasma outlet line 34) after the fluid has been separated into concentrated fluid and plasma.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the concentrated fluid (which may be cellular blood components) away from the membrane 50 to exit the blood separation chamber 28 via the side outlet 54, while the separated plasma passes through the membrane 50 toward the central axis of the housing 48 to exit the blood separation chamber 28 via the bottom outlet 56. It should be understood that the present disclosure is not limited to a particular blood separation chamber and that the illustrated and described blood separation chamber 28 is merely exemplary. For example, in other embodiments, a centrifugal device that separates fluid components based on density, rather than size, may be employed to separate a plasma-containing fluid into plasma and a concentrated fluid.

Figure 8A:
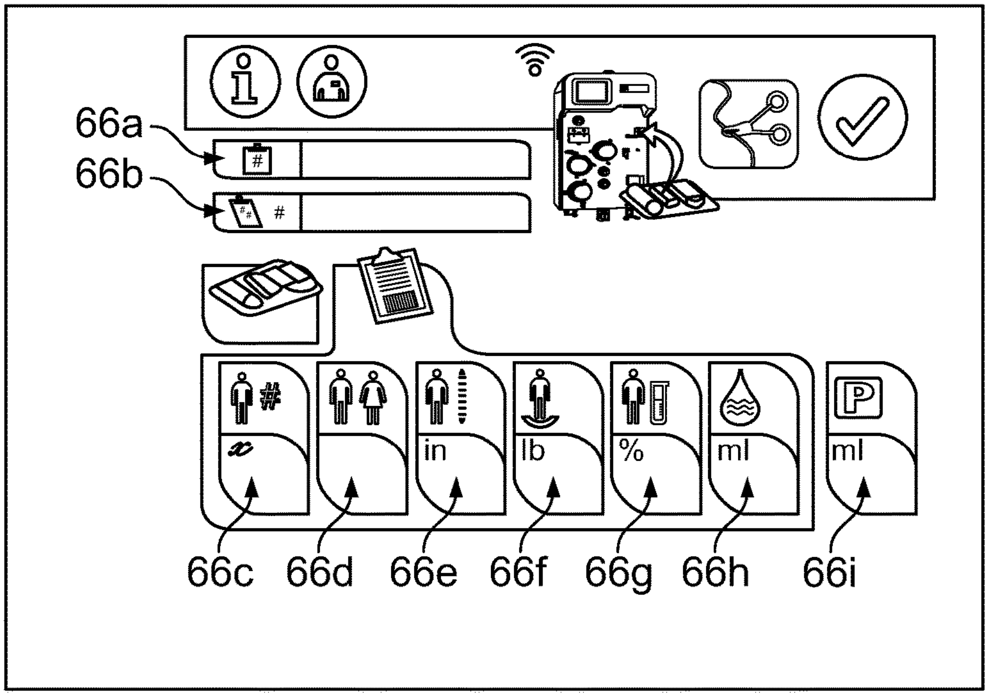
FIGS. 8A, 8B, 9A, and 9B illustrate exemplary screens that may be presented on a display or data entry device of the blood separation device of FIG. 1.
Figure 8B:
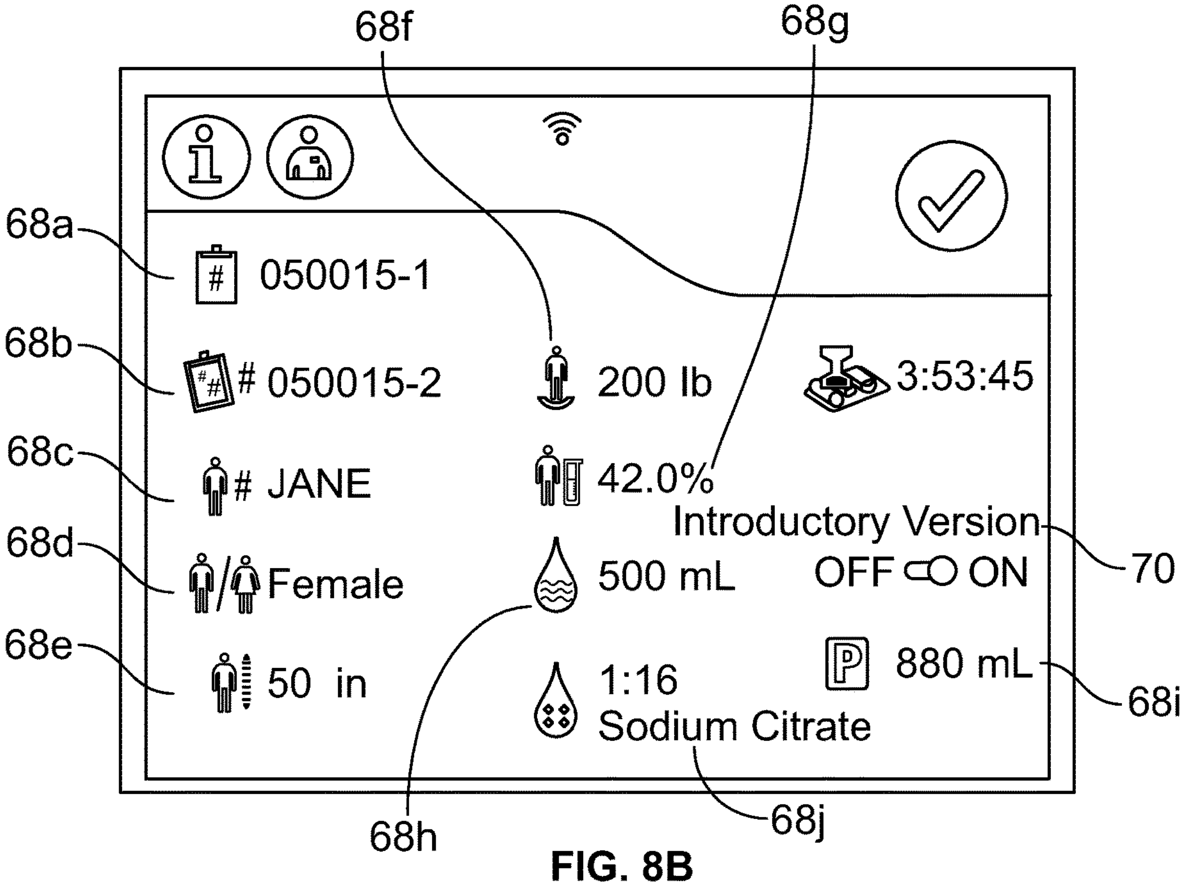

The device 10 may include alternative and/or additional components without departing from the scope of the present disclosure. For example, the illustrated device 10 includes a hemoglobin detector or optical sensor assembly 62 associated with the plasma outlet line 34, a blood cell weigh scale associated with the reservoir 32 and a plasma weight scale associated with the separated plasma container 38 of the fluid flow circuit 12. The illustrated device 10 also includes a data entry device 64 configured as a touch screen for inputting information into the controller 16 and displaying the input information or information originating from the controller 16. While a touch screen is illustrated (with FIGS. 8A and 8B showing exemplary images that may be displayed on the touch screen), it should be understood that a differently configured data entry device (e.g., a barcode reader) may also be employed without departing from the scope of the present disclosure.

According to one method of using the illustrated blood separation system, a plasma-containing fluid is drawn from a fluid source into the blood separation chamber 28 during a draw phase or mode (FIG. 5), where it is separated into concentrated fluid and separated plasma. The separated plasma is retained by the device 10 (e.g., within the separated plasma container 38 of the fluid flow circuit 12), while the concentrated fluid is returned to a fluid recipient during a return or reinfusion phase or mode (FIG. 6). In one embodiment, the draw and return phases are repeatedly alternated (drawing from the fluid source, separating the fluid into plasma and concentrated fluid, and then returning the concentrated fluid to the fluid recipient) until a target (e.g., a collected amount of separated plasma) is achieved. All of the draw phases and all of the return phases may be identical or may differ from each other. For example, a final draw phase may draw less fluid from the fluid source than the previous draw phases and a final return phase may infuse a combination of concentrated fluid and replacement fluid to the fluid recipient, whereas the previous return phases return only concentrated fluid to the fluid recipient.

FIG. 7 shows an exemplary phase or mode in which replacement fluid (e.g., saline) is directed to the fluid recipient, either alone or with an amount of concentrated fluid. In the phase of FIG. 7, the clamp or valve 36*d* associated with the replacement fluid line 40 is opened to allow replacement fluid to flow out of the replacement fluid source 42. The clamp or valve 36*a* associated with the draw branch 22*a* of the source/recipient access line 22 may be in a closed condition to prevent fluid flow therethrough, such that the replacement fluid is directed into the blood separation chamber 28. The replacement fluid is pulled out of the blood separation chamber 28 and into the concentrated fluid reservoir 32 by operation of the pump 20*c* associated with the concentrated fluid outlet line 30. If there is any concentrated fluid in the concentrated fluid reservoir 32, then the replacement fluid mixes with the concentrated fluid prior to being pumped to the fluid recipient by the pump 20*a* associated with the source/recipient access line 22, otherwise the replacement fluid alone may be pumped to the fluid recipient. In one embodiment, the replacement fluid return mode of FIG. 7 is carried out only once, as a final return phase (e.g., when the amount of concentrated fluid in the concentrated fluid reservoir 32 is at a sufficiently low level) in which a mixture of concentrated fluid and replacement fluid is returned to the fluid recipient. This may be advantageous to ensure that all of the concentrated fluid in the concentrated fluid reservoir 32 (along with any remaining in the blood separation chamber 28) is rinsed out of the concentrated fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the blood separation chamber 28 and the concentrated fluid reservoir 32 if the replacement fluid is being pumped to a fluid recipient earlier in the procedure. In this case, the clamp or valve 36*d* associated with the replacement fluid line 40 and the clamp or valve 36*a* associated with the draw branch 22*a* of the source/recipient access line 22 may be opened to allow fluid flow therethrough, with the clamp or valve 36*b* associated with the reinfusion branch 22*b* in a closed condition to prevent fluid flow therethrough. The pump 20*a* associated with the source/recipient access line 22 may be activated (with the other two pumps 20*b* and 20*c* inactive) to draw replacement fluid out of the replacement fluid source 42 and through the replacement fluid line 40, the draw branch 22*a*, and finally the source/recipient access line 22 to the fluid recipient.

The illustrated fluid flow circuit 12 and procedure are a "single-needle" variation, with the same blood source access (e.g., a needle) being used to both draw blood from a blood source and return fluid to the blood source. In other embodiments, two blood source/recipient accesses are incorporated into the fluid flow circuit, which allows for a "double-needle" variation of the procedure in which blood may be drawn from a blood source (via a first needle or blood source access) at the same time that fluid is conveyed to the blood source or other recipient (via a second needle or recipient access). It should be understood that the present disclosure is not limited to either a single- or double-needle procedure or to any particular method of blood separation (e.g., via centrifugation or spinning membrane-type separator) or to any particular separation procedure (e.g., separation of blood into plasma and cellular blood components or separation of blood into plasma, buffy coat, and red blood cells).

Execution of a blood separation procedure by the controller 16 will depend upon data received by the controller 16, which is typically received from a data management system or entered by an operator using the data entry device 64. FIGS. 8A and 8B show exemplary images that may be displayed on a screen of a data entry device 64, with FIG. 8A showing a pre-processing image that requests various information from the operator. The exemplary screen of FIG. 8A includes various fields 66*a*-66*i* for receiving and displaying data entered by the operator, which may include: a first field 66*a* for providing a procedure ID, a second field 66*b* for providing a donation setup ID, a third field 66*c* for providing a blood source ID, a fourth field 66*d* for providing a sex of a human blood source, a fifth field 66*e* for providing a height of a human blood source, a sixth field 66*f* for providing a weight of a human blood source, a seventh field 66*g* for providing information regarding the blood of the blood source (e.g., a hemoglobin or hematocrit level or platelet pre-count), an eighth field 66*h* for providing a procedure parameter (such as target saline volume), and a ninth field 66*i* for providing an additional procedure parameter (such as target plasma collection volume or a target combined volume of collected plasma and anticoagulant). It should be understood that the data requested in the screen of FIG. 8A is merely exemplary and that a data entry device 64 may request additional or different information from an operator.

The image of FIG. 8B may be considered as a summary or confirmation screen, which displays the various data entries after they have all been entered by the operator using the screen of FIG. 8A. In addition to nine fields 68*a*-68*i* that correspond to the nine fields of 66*a*-66*i* (respectively), the screen of FIG. 8B includes an additional field 68*j* that does not display data entered by the operator, but rather displays a center- or admin-configured value, which is an anticoagulant to whole blood ratio in the illustrated example. Field 68*j* may instead display a calculated value derived from one or more of the entries provided by the operator using the data entry device 64, or the screen may be provided with one or more additional fields each presenting a different calculated value. This calculated value may be any of a number of possible values including, without limitation, an anticoagulant to whole blood ratio, body mass index of a human source (which may be calculated using the height and weight of the blood source), the total blood volume of the source (which may be estimated using the height and weight of a human blood source according to a known approach, such as use of the Lemmens-Bernstein-Brodsky equation, or a novel approach), the total red blood cell or plasma volume of the source, the extracellular fluid volume of the source, and the estimated time required to complete the procedure. It is within the scope of the present disclosure for a summary or confirmation screen to display a plurality of calculated values and/or for multiple summary or confirmation screens (each displaying one or more calculated values) to be presented.

The controller 16 receives the data from the data management system or entered by the operator using the data entry device 64, along with calculating or being provided with the calculated values. The controller 16 then controls the other components of the device 10 to execute a selected blood separation procedure.

According to an aspect of the present disclosure, the controller 16 is configured to implement two different versions of the same blood separation procedure, which versions are referred to herein as an “introductory” or “gentle” version and a “standard” version. The “introductory” version of a given procedure is intended to be implemented for a blood source that may not be suited for the “standard” version for any of a number of reasons, with the “introductory” version being intended to improve donor tolerance of the procedure by reducing minor/moderate reactions. According to another aspect of the present disclosure, it is possible for a blood source to “graduate” from the “introductory” version of a procedure, by successfully undergoing the “introductory” version of the procedure one or more times in order to establish that they are ready for the “standard” version. Once such a blood source has established that they are ready for the “standard” version of the procedure, that version may be implemented for that blood source for future iterations of the procedure.

The “introductory” version of a blood separation procedure may differ from the “standard” version in any of a number of ways. For example, the separation efficiency of the blood separation device 10 may be greater in the “standard” version than in the “introductory” version. In the above-described procedure (in which cellular blood components are separated from plasma), this difference would take the form of a relatively high blood cell separation efficiency when implementing the “standard” version of the procedure and a lower blood cell separation efficiency when implementing the “introductory” version of the procedure.

According to another possible difference, a greater percentage of the blood and/or red blood cells of the blood source may be present in the fluid flow circuit 12 at any particular time during implementation of the “standard” version of a procedure than during implementation of the “introductory” version. For example, as described above, it is possible to calculate the total blood volume or pre-procedure red blood cell volume of a blood source. When implementing the “introductory” version of a procedure, the controller 16 may actuate the other components of the blood separation device 10 to allow for no more than 14% of the calculated total blood volume and/or pre-procedure red blood cell volume of the blood source to be present in the fluid flow circuit 12 at any particular time. When implementing the “standard” version of the same procedure, the controller 16 may actuate the other components of the blood separation device 10 to allow for a greater percentage of the calculated total blood volume and/or pre-procedure red blood cell volume of the blood source (e.g., up to 16%) to be present in the fluid flow circuit 12 at any particular time. Alternatively, different limits may be placed on the volume of blood or red blood cells of a blood source that may be present in the fluid flow circuit 12 at any particular time during implementation of a procedure, with there being a greater limit (e.g., 250 ml of red blood cells or 600 ml of blood) for a “standard” version of a procedure than for an “introductory” version (e.g., 200 ml of red blood cells or 500 ml of blood).

Figure 9A:
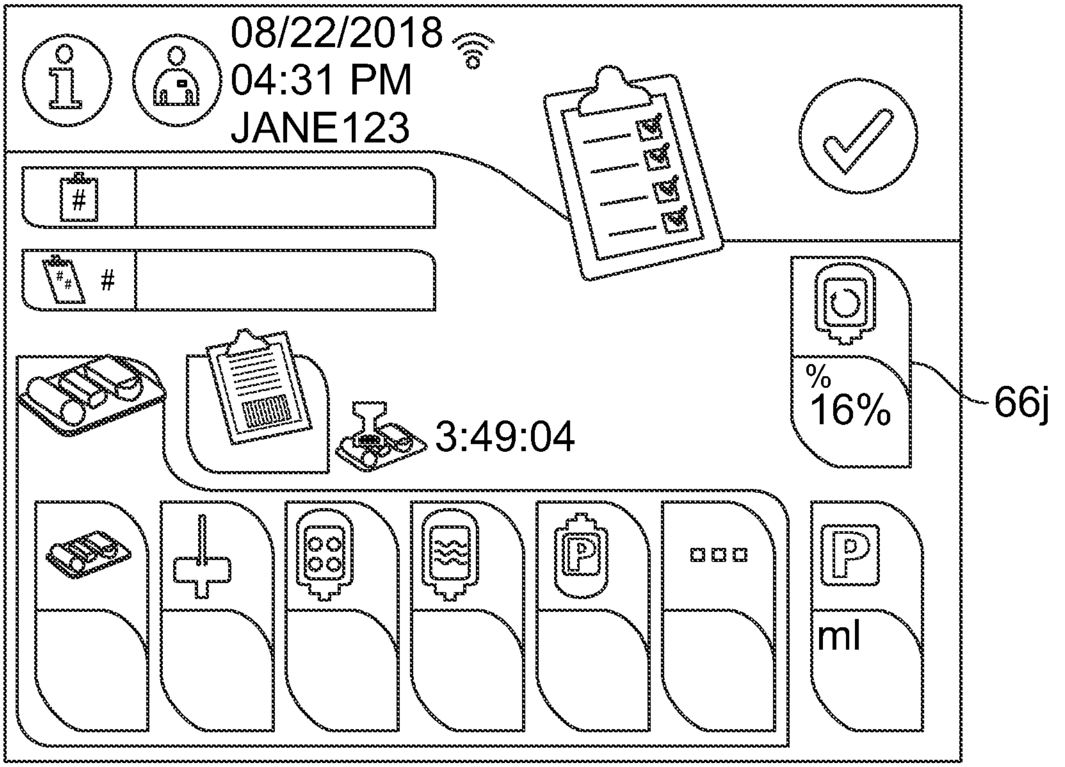

It should be understood that 14% and 16% are merely exemplary and that other percentages may be employed as limits for the “introductory” and “standard” versions of a procedure. According to one aspect of the present disclosure, a blood draw center or facility may be enabled to set a range of percentages that may be used during a procedure. For example, a blood draw center may set a range of 12-16% of the calculated total blood and/or pre-procedure red blood cell volume of a blood source for the maximum allowable volume of blood and/or red blood cells that may be present in a fluid flow circuit 12 at any particular time during a procedure. An operator may then instruct the controller 16 (e.g., using the data entry device 64) which percentage within the predetermined range to employ when executing one of the versions of a blood separation procedure, as shown in FIG. 9A at icon 66*j*.

Figure 9B:
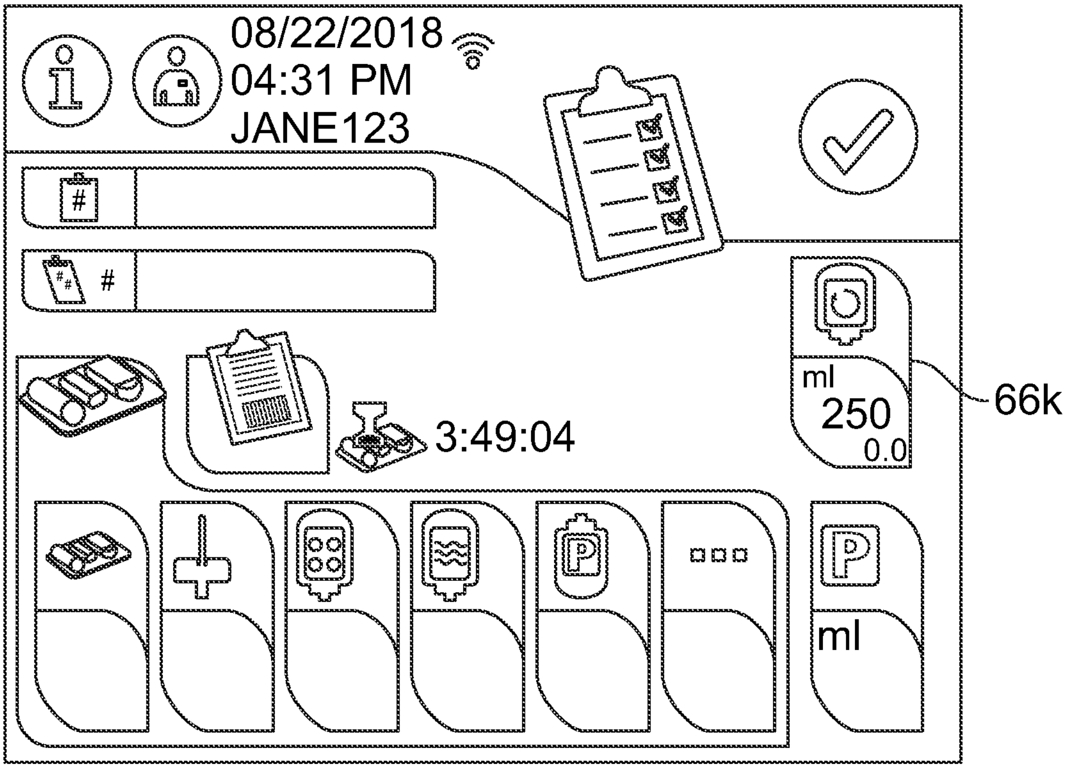

Similarly, it should be understood that 200 ml and 250 ml of red blood cells and 500 ml and 600 ml of blood are merely exemplary and that other volumes may be employed as limits for the “introductory” and “standard” versions of a procedure. According to one aspect of the present disclosure, a blood draw center or facility may be enabled to set a range of maximum volumes that may be used during a procedure. For example, a blood draw center may set a range of 150-250 ml for the maximum allowable volume of red blood cells and/or 450-600 ml for the maximum allowable volume of blood that may be present in a fluid flow circuit 12 at any particular time during a procedure. An operator may then instruct the controller 16 (e.g., using the data entry device 64) which volume within the predetermined range to employ when executing one of the versions of a blood separation procedure, as shown in FIG. 9B at icon 66*k*.

According to yet another possible difference, a relatively large blood separation chamber 28 (allowing for a greater extracorporeal fluid volume) may be employed when implementing the “standard” version of a blood separation procedure, with a relatively small blood separation chamber 28 (allowing for a smaller extracorporeal fluid volume) may be employed when implementing the “introductory” version of the same procedure. The particular size and configuration of such “standard” and “introductory” blood separation chambers may vary without departing from the scope of the present disclosure. However, in an exemplary embodiment, the sizes of the “standard” and “introductory” blood separation chambers may be selected based on the allowable extracorporeal fluid volume for the associated version of the procedure (e.g., with an “introductory” blood separation chamber being configured such that no more than 14% of the blood of a blood source can be present in the fluid flow circuit 12 at any one time when implementing the “introductory” version of a procedure and with a “standard” blood separation chamber being configured such that up to 16% of the blood of a blood source can be present in the fluid flow circuit 12 at any one time during a “standard” version of that same procedure).

According to another possible difference, one or more stages of a procedure may be enhanced when implementing the “standard” version of a blood separation procedure. For example, the blood draw stage (as shown in FIG. 5) executed during a “standard” version of a blood separation procedure may have a different duration than the same stage during an “introductory” version of the same procedure. The controller 16 may also (or alternatively) actuate the pump system to draw blood from the blood source at a different (typically higher) rate during a “standard” version of the blood draw stage compared to the blood draw rate during an “introductory” version. This may include different minimum and/or maximum draw rates in each version of the procedure. In general, more blood may be drawn from the blood source during the blood draw stage of a “standard” version of a procedure than during the blood draw stage of an “introductory” version of the same procedure. In embodiments in which multiple blood draw stages are executed (typically “single-needle” procedures), it may be advantageous for the first blood draw stage of an “introductory” version of a procedure to have a particularly low draw rate (for donor comfort), with the draw rate increasing in one or more subsequent blood draw stages.

Similarly, a fluid return stage (as shown in FIGS. 6 and 7) executed during a "standard" version of a blood separation procedure may have a different duration than the same stage during an "introductory" version of the same procedure. The controller 16 may also (or alternatively) actuate the pump system to convey fluid to a recipient (e.g., the blood source) at a different rate during a "standard" version of the fluid return stage compared to the fluid return rate during an "introductory" version. This may include different minimum and/or maximum return rates in each version of the procedure. In general, more fluid may be conveyed to the recipient during the fluid return stage of a "standard" version of a procedure than during the fluid return stage of an "introductory" version of the same procedure (as more blood may be drawn from the source during the "standard" version). In embodiments in which multiple fluid returns stages are executed (typically "single-needle" procedures), it may be advantageous for the first fluid return stage of an "introductory" version of a procedure to have a particularly low return rate (for donor comfort), with the return rate increasing in one or more subsequent fluid return stages.

According to one aspect of the present disclosure, the parameters of one or both versions of the procedure may be configured upon the device 10 being installed and set up and/or may be adjusted by an operator before or at the beginning of a procedure. This may include the ranges or limits on the parameters that may be selected by an operator (e.g., if an operator is limited to selecting a maximum extracorporeal blood volume from a range of values).

The criteria by which a blood source is designated for the "introductory" version of a blood separation procedure or the "standard" version may vary without departing from the scope of the present disclosure. This screening process may involve a blood source being designated as qualified for the "introductory" version, qualified for the "standard" version, not qualified for the "introductory" version, or not qualified for the "standard" version. By way of example, the age of a blood source may be a factor in determining which version of a blood separation procedure to implement, with the "introductory" version tending to be more suitable for being especially young and especially old blood sources. An additional or alternative factor may be the weight of a blood source, with the "introductory" version tending to be more suitable for lower weight blood sources. The sex of a blood source may be another factor (which may be considered together with other factors or independently), with the "introductory" version more frequently being suitable for female blood sources. Yet another factor may be the day-of-condition of the blood source (e.g., if there is anything about the status of the blood source on the day of a procedure which suggests that a more gentle version may be advisable).

Yet another consideration is whether the blood separation procedure (or a comparable procedure) was previously implemented for the blood source. If the blood source has never undergone the procedure (or a comparable procedure), the "introductory" version of the procedure may be more suitable than the "standard" version. If the blood source has previously undergone the procedure (or a comparable procedure), it may be advantageous to consider the number of times that blood has been drawn from the blood source, which may include the number of times that blood has been drawn from the blood source in a period of time (e.g., to assess whether the blood source is an active and regular participant or if their participation has recently lapsed) and/or the average frequency or number of times that blood has been drawn from the blood source over the relevant time period.

The blood draw history of the blood source may be implemented as a factor in any of a number of ways. In one embodiment, the "history" factor may be treated as a status, with a blood source being categorized as "new" or "lapsed" or "regular," for example. A blood source who has never undergone a particular procedure (or a comparable procedure) may be categorized as a "new" blood source. A blood source who has previously undergone a particular procedure (or a comparable procedure) in the past, but not sufficiently recently (or not recently on a sufficiently regular basis) may be categorized as a "lapsed" blood source. A blood source who has recently and regularly undergone a particular procedure (or a comparable procedure) may be categorized as a "regular" blood source. The different statuses may be given different numerical values or "points" by the controller 16 (e.g., 0 for a "new" blood source, 1 for a "lapsed" blood source, and 2 for a "regular" blood source) when determining which version of a blood separation procedure to implement, with a blood source having a "regular" status being more likely than a "lapsed" or "new" blood source to be considered suitable for implementation of the "standard" version (on account of having more "points").

In another embodiment, the "history" factor may be treated as a number equal to the number of times that blood has been previously drawn from the blood source or the number of times that the blood source has undergone a particular procedure (or a comparable procedure). If different types of procedures are included in the count, certain procedures (e.g., ones that are the same as the particular procedure to be implemented) may be given a greater numerical value or weight than other procedures (e.g., ones that are similar to, but different from, the procedure to be implemented). Similar to the embodiment in which the "history" factor is treated as a status, a blood source who has more frequently undergone a particular procedure (or comparable procedures) may be more likely to qualify for the "standard" version of a blood separation procedure than a less experienced blood source on account of having more "points" or progress towards a qualifying threshold value.

If multiple factors (e.g., the age, sex, and blood draw history of a blood source) are considered when determining which version of a procedure to implement, they may be given the same or different weights. For example, it may be the case that the blood draw history of a blood source may be more relevant (and thus be entitled to more weight) than the age and sex of the blood source. If a blood source is of an age and sex typically suited for the "introductory" version of a procedure, those factors may be outweighed by the blood source having a history of successfully undergoing the "standard" version of the procedure (or having successfully undergone similar blood separation procedures).

As some of the above factors may change during the lifetime of a blood source, they may be reassessed periodically to determine whether a subsequent blood separation procedure should be executed according to the "introductory" version or the "standard" version. Indeed, while it may be more typical for a blood source to "graduate" from the "introductory" version of a procedure to the "standard" version (e.g., by undergoing the "introductory" version of the procedure a certain number of times), it is also possible for a blood source to be transitioned from the "standard" version to the "introductory" version (e.g., if the blood source undergoes a significant weight loss).

The determination as to which version of a blood separation procedure to implement (including whether to change a blood source from one version to the other) may be made in any of a number of ways. For example, based on information provided to it (e.g., by an operator via the data entry device 64 or via a data management system), the controller 16 may determine which version of a procedure to implement and then proceed to implement that version of the procedure without input from an operator. In another embodiment, the controller 16 may provide the operator with a recommended version of the procedure, with the operator having the option of either implementing the recommended version or a different version. This may include the operator being provided with an icon 70 (FIG. 8B) or button to manipulate to initiate a selected version of a procedure, with the appropriate parameters (e.g., draw and return rates, volume of blood to be processed each cycle, maximum allowable extracorporeal blood volume, maximum allowable extracorporeal red blood cell volume, etc.) being automatically implemented by the controller 16. In yet another embodiment, the operator may be enabled to select (e.g., using an icon 70 or button or the like) the version of the procedure to implement without receiving input from the controller 16. In still another embodiment, some other authority (e.g., a "front desk" operator or central controller) may be enabled to make the determination of which version of a procedure to implement. Instructing the controller 16 to execute one version of a procedure or another may be as simple as setting a single flag value in a procedure setup file or may be implemented in any other way without departing from the scope of the present disclosure.

While "introductory" and "standard" versions of a blood separation procedure are described herein, it should be understood that the present disclosure is not limited to execution of an "introductory" or "gentle" version of a procedure and a "standard" version of the same procedure. For example, two "standard" versions of a blood separation procedure may available, with the two versions being substantially equivalent alternatives that differ in some way, rather than one version being presented as a "gentle" version of the procedure. Indeed, the manner in which two versions of a particular blood separation procedure differ may vary without departing from the scope of the present disclosure.

While implementation of "introductory" and "standard" versions of a given blood separation procedure is described above as being executed by a single blood separation device 10, it should be understood that multiple blood separation devices (which may be similarly or differently configured) may instead be employed. According to this approach, a first device may be configured to execute a first version of the procedure (e.g., the "introductory" version), with a second device being configured to execute the second version of the procedure (e.g., the "standard" version). Thus, a blood source may "graduate" from the first or "introductory" version of the procedure to the second or "standard" version by transitioning from use of the first device to use of the second device.

Additionally, while "introductory" and "standard" versions of a given blood separation procedure are described above, it should be understood that a single blood separation device may be configured to implement three or more different versions of a particular procedure (e.g., an "introductory" version, an "intermediate" version, and a "standard" version). Similarly, if three or more different versions of a particular procedure are available, the same number of similarly or differently configured blood separation devices may be provided, with each configured to implement one of the versions of the procedure.

Aspects

Aspect 1. A method of implementing a blood separation procedure, comprising: selecting a first blood separation device configured to execute a first version of a blood separation procedure and a second blood separation device configured to execute a second version of the blood separation procedure or a single blood separation device configured to execute the first and second versions of the blood separation procedure; determining whether a blood source is qualified for the first version of the blood separation procedure or the second version of the blood separation procedure and/or determining whether a blood source is not qualified for the first version of the blood separation procedure or the second version of the blood separation procedure; implementing the first version of the blood separation procedure for the blood source upon determining that the blood source is qualified for the first version of the blood separation procedure and/or upon determining that the blood source is not qualified for the second version of the blood separation procedure; and implementing the second version of the blood separation procedure for the blood source upon determining that the blood source is qualified for the second version of the blood separation procedure and/or upon determining that the blood source is not qualified for the first version of the blood separation procedure.

Aspect 2. The method of Aspect 1, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing an age of the blood source.

Aspect 3. The method of any one of the preceding Aspects, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing a weight of the blood source.

Aspect 4. The method of any one of the preceding Aspects, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing a sex of the blood source.

Aspect 5. The method of any one of the preceding Aspects, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing whether the blood separation procedure was previously implemented for the blood source.

Aspect 6. The method of Aspect 5, wherein said assessing whether the blood separation procedure was previously implemented for the blood source includes categorizing the blood source as a "new" blood source when the blood separation procedure was never previously implemented for the blood source.

Aspect 7. The method of any one of Aspects 5-6, wherein said assessing whether the blood separation procedure was previously implemented for the blood source includes categorizing the blood source as a "lapsed" blood source when a predetermined amount of time has elapsed since the blood separation procedure was last implemented for the blood source.

Aspect 8. The method of any one of Aspects 5-7, wherein said assessing whether the blood separation procedure was previously implemented for the blood source includes categorizing the blood source as a "regular" blood source when the blood separation procedure has been implemented for the blood source more recently than a predetermined amount of time.

Aspect 9. The method of any one of Aspects 5-8, wherein said assessing whether the blood separation procedure was previously implemented for the blood source includes assigning one of a plurality of statuses to the blood source based at least in part on whether the blood separation procedure was previously implemented for the blood source, and each of the plurality of statuses is given a different value or weight when determining whether the blood source is qualified for the first version of the blood separation procedure or the second version of the blood separation procedure and/or determining whether the blood source is not qualified for the first version of the blood separation procedure or the second version of the blood separation procedure.

Aspect 10. The method of any one of the preceding Aspects, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing the number of times that blood has been drawn from the blood source.

Aspect 11. The method of Aspect 10, wherein said assessing the number of times that blood has been drawn from the blood source includes assessing the number of times that blood has been drawn from the blood source in a period of time.

Aspect 12. The method of Aspect 11, wherein said assessing the number of times that blood has been drawn from the blood source includes assessing the average number of times that blood has been drawn from the blood source in the period of time.

Aspect 13. The method of any one of Aspects 10-12, wherein said assessing the number of times that blood has been drawn from the blood source includes determining the type of a previous blood draw procedure implemented for the blood source during which blood was drawn from the blood source.

Aspect 14. The method of Aspect 13, wherein said determining the type of the previous blood draw procedure includes selecting from a plurality of types of blood draw procedures and giving different values or weights to at least two different types of blood draw procedures when determining whether the blood source is qualified for the first version of the blood separation procedure or the second version of the blood separation procedure and/or determining whether a blood source is not qualified for the first version of the blood separation procedure or the second version of the blood separation procedure.

Aspect 15. The method of Aspect 14, wherein a first one of said types of blood draw procedures is the blood separation procedure to be implemented for the blood source, a second one of said types of blood draw procedures is not the blood separation procedure to be implemented for the blood source, and a greater value or weight is given to said first type of blood draw procedure than to said second type of blood draw procedure when determining whether the blood source is qualified for the first version of the blood separation procedure or the second version of the blood separation procedure and/or determining whether a blood source is not qualified for the first version of the blood separation procedure or the second version of the blood separation procedure.

Aspect 16. The method of any one of the preceding Aspects, wherein the blood separation procedure includes separating blood from the blood source into cellular blood components and plasma, and conveying at least a portion of the cellular blood components to a recipient.

Aspect 17. The method of Aspect 16, wherein the blood source is the recipient.

Aspect 18. The method of any one of Aspects 16-17, wherein a blood cell separation efficiency of the first version of the blood separation procedure is different from a blood cell separation efficiency of the second version of the blood separation procedure.

Aspect 19. The method of any one of Aspects 16-18, further comprising determining a pre-procedure red blood cell volume of the blood source, wherein implementing the blood separation procedure includes separating blood from the blood source in a fluid flow circuit, a volume of red blood cells less than a selected percentage or maximum volume of the pre-procedure red blood cell volume is allowed to be present in the fluid flow circuit at any time when implementing the first version of the blood separation procedure, and a volume of red blood cells different from said selected percentage or maximum volume of the pre-procedure red blood cell volume is allowed to be present in the fluid flow circuit at at least one time when implementing the second version of the blood separation procedure.

Aspect 20. The method of any one of Aspects 16-18, further comprising determining a total blood volume of the blood source, wherein implementing the blood separation procedure includes separating blood from the blood source in a fluid flow circuit, a volume of blood less than a selected percentage or maximum volume of the total blood volume is allowed to be present in the fluid flow circuit at any time when implementing the first version of the blood separation procedure, and a volume of blood different from said selected percentage or maximum volume of the total blood volume is allowed to be present in the fluid flow circuit at at least one time when implementing the second version of the blood separation procedure.

Aspect 21. The method of any one of the preceding Aspects, wherein implementing the first version of the blood separation procedure includes separating blood from the blood source in a first blood separation chamber, and implementing the second version of the blood separation procedure includes separating blood from the blood source in a second blood separation chamber having a different volume than the first blood separation chamber.

Aspect 22. The method of any one of the preceding Aspects, wherein implementing the first version of the blood separation procedure includes executing an first blood draw phase having a duration, a draw rate, and a blood draw volume, and implementing the second version of the blood separation procedure includes executing a second blood draw phase having a different duration, draw rate, and/or blood draw volume than said first blood draw phase.

Aspect 23. The method of any one of the preceding Aspects, wherein implementing the first version of the blood separation procedure includes executing a first fluid return phase having a duration, a return rate, and a fluid return volume, and implementing the second version of the blood separation procedure includes executing a second fluid return phase having a different duration, return rate, and/or fluid return volume than said first fluid return phase.

Aspect 24. A blood separation device, comprising: a pump system; a clamp system; a separation actuator; and a controller programmed with first and second versions of a blood separation procedure in which the pump system, the clamp system, and the separation actuator are actuated to draw blood from a blood source, separate the blood into at least two blood components, and convey at least a portion of one of said blood components to a recipient, wherein the controller is configured to determine or be instructed that the blood source is qualified for the first version of the blood separation procedure or the second version of the blood separation procedure and/or determine or be instructed that the blood source is not qualified for the first version of the blood separation procedure or the second version of the blood separation procedure, implement the first version of the blood separation procedure for the blood source upon determining or being instructed that the blood source is qualified for the first version of the blood separation procedure and/or upon determining or being instructed that the blood source is not qualified for the second version of the blood separation procedure, and implement the second version of the blood separation procedure for the blood source upon determining or being instructed that the blood source is qualified for the second version of the blood separation procedure and/or upon determining or being instructed that the blood source is not qualified for the first version of the blood separation procedure.

Aspect 25. The blood separation device of Aspect 24, wherein implementation of the first vs. second version of the blood separation procedure is based at least in part on an age of the blood source.

Aspect 26. The blood separation device of any one of Aspects 24-25, wherein implementation of the first vs. second version of the blood separation procedure is based at least in part on a weight of the blood source.

Aspect 27. The blood separation device of any one of Aspects 24-26, wherein implementation of the first vs. second version of the blood separation procedure is based at least in part on a sex of the blood source.

Aspect 28. The blood separation device of any one of Aspects 24-27, wherein implementation of the first vs. second version of the blood separation procedure is based at least in part on whether the blood separation procedure was previously implemented for the blood source.

Aspect 29. The blood separation device of Aspect 28, wherein assessing whether the blood separation procedure was previously implemented for the blood source includes categorizing the blood source as a "new" blood source when the blood separation procedure was never previously implemented for the blood source.

Aspect 30. The blood separation device of any one of Aspects 28-29, wherein assessing whether the blood separation procedure was previously implemented for the blood source includes categorizing the blood source as a "lapsed" blood source when a predetermined amount of time has elapsed since the blood separation procedure was last implemented for the blood source.

Aspect 31. The blood separation device of any one of Aspects 28-30, wherein assessing whether the blood separation procedure was previously implemented for the blood source includes categorizing the blood source as a "regular" blood source when the blood separation procedure has been implemented for the blood source more recently than a predetermined amount of time.

Aspect 32. The blood separation device of any one of Aspects 28-31, wherein assessing whether the blood separation procedure was previously implemented for the blood source includes assigning one of a plurality of statuses to the blood source based at least in part on whether the blood separation procedure was previously implemented for the blood source, and each of the plurality of statuses is given a different value or weight when determining whether the blood source is qualified for the first version of the blood separation procedure or the second version of the blood separation procedure and/or determining whether the blood source is not qualified for the first version of the blood separation procedure or the second version of the blood separation procedure.

Aspect 33. The blood separation device of any one of Aspects 24-32, wherein implementation of the first vs. second version of the blood separation procedure is based at least in part on the number of times that blood has been drawn from the blood source.

Aspect 34. The blood separation device of Aspect 33, wherein said number of times that blood has been drawn from the blood source includes the number of times that blood has been drawn from the blood source in a period of time.

Aspect 35. The blood separation device of Aspect 34, wherein said number of times that blood has been drawn from the blood source includes the average number of times that blood has been drawn from the blood source in the period of time.

Aspect 36. The blood separation device of any one of Aspects 33-35, wherein assessing the number of times that blood has been drawn from the blood source includes determining the type of a previous blood draw procedure implemented for the blood source during which blood was drawn from the blood source.

Aspect 37. The blood separation device of Aspect 36, wherein determining the type of the previous blood draw procedure includes selecting from a plurality of types of blood draw procedures and giving different values or weights to at least two different types of blood draw procedures when determining whether the blood source is qualified for the first version of the blood separation procedure or the second version of the blood separation procedure and/or determining whether a blood source is not qualified for the first version of the blood separation procedure or the second version of the blood separation procedure.

Aspect 38. The blood separation device of Aspect 37, wherein a first one of said types of blood draw procedures is the blood separation procedure to be implemented for the blood source, a second one of said types of blood draw procedures is not the blood separation procedure to be implemented for the blood source, and a greater value or weight is given to said first type of blood draw procedure than to said second type of blood draw procedure when determining whether the blood source is qualified for the first version of the blood separation procedure or the second version of the blood separation procedure and/or determining whether a blood source is not qualified for the first version of the blood separation procedure or the second version of the blood separation procedure.

Aspect 39. The blood separation device of any one of Aspects 24-38, wherein the blood separation procedure includes separating blood from the blood source into cellular blood components and plasma, and conveying at least a portion of the cellular blood components to a recipient.

Aspect 40. The blood separation device of Aspect 39, wherein the blood source is the recipient.

Aspect 41. The blood separation device of any one of Aspects 39-40, wherein a blood cell separation efficiency of the first version of the blood separation procedure is different from a blood cell separation efficiency of the second version of the blood separation procedure.

Aspect 42. The blood separation device of any one of Aspects 39-41, wherein the controller is further configured to determine or be provided with a pre-procedure red blood cell volume of the blood source, implementing the blood separation procedure includes separating blood from the blood source in a fluid flow circuit, a volume of red blood cells less than a selected percentage of the pre-procedure red blood cell volume is allowed to be present in the fluid flow circuit at any time when implementing the first version of the blood separation procedure, and a volume of red blood cells different from said selected percentage of the pre-procedure red blood cell volume is allowed to be present in the fluid flow circuit at at least one time when implementing the second version of the blood separation procedure.

Aspect 43. The blood separation device of any one of Aspects 39-41, wherein the controller is further configured to determine or be provided with a total blood volume of the blood source, implementing the blood separation procedure includes separating blood from the blood source in a fluid flow circuit, a volume of blood less than a selected percentage of the total blood volume is allowed to be present in the fluid flow circuit at any time when implementing the first version of the blood separation procedure, and a volume of blood different from said selected percentage of the total blood volume is allowed to be present in the fluid flow circuit at at least one time when implementing the second version of the blood separation procedure.

Aspect 44. The blood separation device of any one of Aspects 24-43, wherein implementing the first version of the blood separation procedure includes separating blood from the blood source in a first blood separation chamber, and implementing the second version of the blood separation procedure includes separating blood from the blood source in a second blood separation chamber having a different volume than the first blood separation chamber.

Aspect 45. The blood separation device of any one of Aspects 24-44, wherein implementing the first version of the blood separation procedure includes executing a first blood draw phase having a duration, a draw rate, and a blood draw volume, and implementing the second version of the blood separation procedure includes executing a second blood draw phase having a different duration, draw rate, and/or blood draw volume than said second blood draw phase.

Aspect 46. The blood separation device of any one of Aspects 24-45, wherein implementing the first version of the blood separation procedure includes executing a first fluid return phase having a duration, a return rate, and a fluid return volume, and implementing the second version of the blood separation procedure includes executing a second fluid return phase having a different duration, return rate, and/or fluid return volume than said first fluid return phase.

Aspect 47. The blood separation device of any one of Aspects 24-46, further comprising a data entry device including a button or icon configured to be manipulated by an operator to instruct the controller to implement the first version of the blood separation procedure.

Aspect 48. The blood separation device of any one of Aspects 24-46, further comprising a data entry device configured to receive entered data regarding a blood source, wherein the controller is configured to determine whether to implement the first vs. second version of the blood separation procedure based at least in part on said entered data.

Aspect 49. A blood separation device, comprising: a pump system; a clamp system; a separation actuator; and a controller configured to actuate the pump system, the clamp system, and the separation actuator to execute a blood separation procedure in which a volume of blood having a volume of red blood cells is present in a fluid flow circuit, wherein the controller is further configured to be instructed of a maximum percentage and/or a maximum volume of a total blood volume of a blood source that may be present in the fluid flow circuit at any one time during said blood separation procedure and/or a maximum percentage and/or a maximum volume of a pre-procedure red blood cell volume of the blood source that may be present in the fluid flow circuit at any one time during said blood separation procedure.

Aspect 50. The blood separation device of Aspect 49, wherein said maximum percentage and/or maximum volume of the total blood volume of the blood source that may be present in the fluid flow circuit at any one time during said blood separation procedure is limited to a predetermined range.

Aspect 51. The blood separation device of Aspect 50, further comprising a data entry device configured to communicate with the controller, wherein the controller is further configured to allow an operator to manipulate the data entry device to select the maximum percentage and/or maximum volume of the total blood volume of the blood source that may be present in the fluid flow circuit at any one time during said blood separation procedure from said predetermined range.

Aspect 52. The blood separation device of any one of Aspects 49-51, wherein said maximum percentage and/or maximum volume of the pre-procedure red blood cell volume of the blood source that may be present in the fluid flow circuit at any one time during said blood separation procedure is limited to a predetermined range.

Aspect 53. The blood separation device of Aspect 52, further comprising a data entry device configured to communicate with the controller, wherein the controller is further configured to allow an operator to manipulate the data entry device to select the maximum percentage and/or maximum volume of the pre-procedure red blood cell volume of the blood source that may be present in the fluid flow circuit at any one time during said blood separation procedure from said predetermined range.

Aspect 54. A computer-implemented method of executing a blood separation procedure using a first blood separation device configured to execute a first version of a blood separation procedure and a second blood separation device configured to execute a second version of the blood separation procedure or a single blood separation device configured to execute the first and second versions of the blood separation procedure, the method comprising: determining whether a blood source is qualified for the first version of the blood separation procedure or the second version of the blood separation procedure and/or determining whether a blood source is not qualified for the first version of the blood separation procedure or the second version of the blood separation procedure; initiating or prompting an operator to initiate the first version of the blood separation procedure for the blood source upon determining that the blood source is qualified for the first version of the blood separation procedure and/or upon determining that the blood source is not qualified for the second version of the blood separation procedure; and initiating or prompting an operator to initiate the second version of the blood separation procedure for the blood source upon determining that the blood source is qualified for the second version of the blood separation procedure and/or upon determining that the blood source is not qualified for the first version of the blood separation procedure.

Aspect 55. The method of Aspect 54, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing an age of the blood source.

Aspect 56. The method of any one of Aspects 54-55, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing a weight of the blood source.

Aspect 57. The method of any one of Aspects 54-56, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing a sex of the blood source.

Aspect 58. The method of any one of Aspects 54-57, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing whether the blood separation procedure was previously implemented for the blood source.

Aspect 59. The method of Aspect 58, wherein said assessing whether the blood separation procedure was previously implemented for the blood source includes categorizing the blood source as a "new" blood source when the blood separation procedure was never previously implemented for the blood source.

Aspect 60. The method of any one of Aspects 58-59, wherein said assessing whether the blood separation procedure was previously implemented for the blood source includes categorizing the blood source as a "lapsed" blood source when a predetermined amount of time has elapsed since the blood separation procedure was last implemented for the blood source.

Aspect 61. The method of any one of Aspects 58-60, wherein said assessing whether the blood separation procedure was previously implemented for the blood source includes categorizing the blood source as a "regular" blood source when the blood separation procedure has been implemented for the blood source more recently than a predetermined amount of time.

Aspect 62. The method of any one of Aspects 58-61, wherein said assessing whether the blood separation procedure was previously implemented for the blood source includes assigning one of a plurality of statuses to the blood source based at least in part on whether the blood separation procedure was previously implemented for the blood source, and each of the plurality of statuses is given a different value or weight when determining whether the blood source is qualified for the first version of the blood separation procedure or the second version of the blood separation procedure and/or determining whether the blood source is not qualified for the first version of the blood separation procedure or the second version of the blood separation procedure.

Aspect 63. The method of any one of Aspects 54-62, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing the number of times that blood has been drawn from the blood source.

Aspect 64. The method of Aspect 63, wherein said assessing the number of times that blood has been drawn from the blood source includes assessing the number of times that blood has been drawn from the blood source in a period of time.

Aspect 65. The method of Aspect 64, wherein said assessing the number of times that blood has been drawn from the blood source includes assessing the average number of times that blood has been drawn from the blood source in the period of time.

Aspect 66. The method of any one of Aspects 63-65, wherein said assessing the number of times that blood has been drawn from the blood source includes determining the type of a previous blood draw procedure implemented for the blood source during which blood was drawn from the blood source.

Aspect 67. The method of Aspect 66, wherein said determining the type of the previous blood draw procedure includes selecting from a plurality of types of blood draw procedures and giving different values or weights to at least two different types of blood draw procedures when determining whether the blood source is qualified for the first version of the blood separation procedure or the second version of the blood separation procedure and/or determining whether a blood source is not qualified for the first version of the blood separation procedure or the second version of the blood separation procedure.

Aspect 68. The method of Aspect 67, wherein a first one of said types of blood draw procedures is the blood separation procedure to be implemented for the blood source, a second one of said types of blood draw procedures is not the blood separation procedure to be implemented for the blood source, and a greater value or weight is given to said first type of blood draw procedure than to said second type of blood draw procedure when determining whether the blood source is qualified for the first version of the blood separation procedure or the second version of the blood separation procedure and/or determining whether a blood source is not qualified for the first version of the blood separation procedure or the second version of the blood separation procedure.

Aspect 69. The method of any one of Aspects 54-68, wherein the blood separation procedure includes separating blood from the blood source into cellular blood components and plasma, and conveying at least a portion of the cellular blood components to a recipient.

Aspect 70. The method of Aspect 69, wherein the blood source is the recipient.

Aspect 71. The method of any one of Aspects 69-70, wherein a blood cell separation efficiency of the first version of the blood separation procedure is different from a blood cell separation efficiency of the second version of the blood separation procedure.

Aspect 72. The method of any one of Aspects 69-71, further comprising determining a pre-procedure red blood cell volume of the blood source, wherein the blood separation procedure includes separating blood from the blood source in a fluid flow circuit, a volume of red blood cells less than a selected percentage or maximum volume of the pre-procedure red blood cell volume is allowed to be present in the fluid flow circuit at any time when executing the first version of the blood separation procedure, and a volume of red blood cells different from said selected percentage or maximum volume of the pre-procedure red blood cell volume is allowed to be present in the fluid flow circuit at at least one time when executing the second version of the blood separation procedure.

Aspect 73. The method of any one of Aspects 69-71, further comprising determining a total blood volume of the blood source, wherein the blood separation procedure includes separating blood from the blood source in a fluid flow circuit, a volume of blood less than a selected percentage or maximum volume of the total blood volume is allowed to be present in the fluid flow circuit at any time when executing the first version of the blood separation procedure, and a volume of blood different from said selected percentage or maximum volume of the total blood volume is allowed to be present in the fluid flow circuit at at least one time when executing the second version of the blood separation procedure.

Aspect 74. The method of any one of Aspects 54-73, wherein the first version of the blood separation procedure includes separating blood from the blood source in a first blood separation chamber, and the second version of the blood separation procedure includes separating blood from the blood source in a second blood separation chamber having a different volume than the first blood separation chamber.

Aspect 75. The method of any one of Aspects 54-74, wherein the first version of the blood separation procedure includes a first blood draw phase having a duration, a draw rate, and a blood draw volume, and the second version of the blood separation procedure includes a second blood draw phase having a different duration, draw rate, and/or blood draw volume than said first blood draw phase.

Aspect 76. The method of any one of Aspects 54-75, wherein the first version of the blood separation procedure includes a first fluid return phase having a duration, a return rate, and a fluid return volume, and the second version of the blood separation procedure includes a second fluid return phase having a different duration, return rate, and/or fluid return volume than said first fluid return phase.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A computer-implemented method of executing a blood separation procedure using a first blood separation device configured to execute a first version of a blood separation procedure and a second blood separation device configured to execute a second version of the blood separation procedure or a single blood separation device configured to execute the first and second versions of the blood separation procedure, the method comprising:

determining whether a blood source is qualified for the first version of the blood separation procedure or the second version of the blood separation procedure and/or determining whether a blood source is not qualified for the first version of the blood separation procedure or the second version of the blood separation procedure;

initiating or prompting an operator to initiate the first version of the blood separation procedure for the blood source upon determining that the blood source is qualified for the first version of the blood separation procedure and/or upon determining that the blood source is not qualified for the second version of the blood separation procedure;

initiating or prompting an operator to initiate the second version of the blood separation procedure for the blood source upon determining that the blood source is qualified for the second version of the blood separation procedure and/or upon determining that the blood source is not qualified for the first version of the blood separation procedure; and either executing the first version of the blood separation procedure for the blood source after initiating or prompting the operator to initiate the first version of the blood separation procedure, or executing the second version of the blood separation procedure for the blood source after initiating or prompting the operator to initiate the second version of the blood separation procedure, wherein each of the first version and the second version of the blood separation procedure has a plurality of procedural parameters, with at least one of the plurality of procedural parameters of the first version of the blood separation procedure being different from the corresponding procedural parameter of the second version of the blood separation procedure, and the blood separation procedure includes the same phases when being executed in the first version and in the second version.

2. The method of claim 1, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing an age of the blood source when the blood source is a living donor or patient.

3. The method of claim 1, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing a weight of the blood source when the blood source is a living donor or patient.

4. The method of claim 1, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing a sex of the blood source when the blood source is a living donor or patient.

5. The method of claim 1, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing whether the blood separation procedure was previously implemented for the blood source.

6. The method of claim 5, wherein said assessing whether the blood separation procedure was previously implemented for the blood source includes categorizing the blood source as a "new" blood source when the blood separation procedure was never previously implemented for the blood source.

7. The method of claim 5, wherein said assessing whether the blood separation procedure was previously implemented for the blood source includes categorizing the blood source as a "lapsed" blood source when a predetermined amount of time has elapsed since the blood separation procedure was last implemented for the blood source.

8. The method of claim 5, wherein said assessing whether the blood separation procedure was previously implemented for the blood source includes categorizing the blood source as a "regular" blood source when the blood separation procedure has been implemented for the blood source more recently than a predetermined amount of time.

9. The method of claim 5, wherein said assessing whether the blood separation procedure was previously implemented for the blood source includes assigning one of a plurality of statuses to the blood source based at least in part on whether the blood separation procedure was previously implemented for the blood source, and each of the plurality of statuses is given a different value or weight when determining whether the blood source is qualified for the first version of the blood separation procedure or the second version of the blood separation procedure and/or determining whether the blood source is not qualified for the first version of the blood separation procedure or the second version of the blood separation procedure.

10. The method of claim 1, wherein said determining whether the blood source is qualified for the first version of the blood separation procedure or the second version of the blood separation procedure and/or determining whether a blood source is not qualified for the first version of the blood separation procedure or the second version of the blood separation procedure includes assessing the number of times that blood has been drawn from the blood source.

11. The method of claim 10, wherein said assessing the number of times that blood has been drawn from the blood source includes assessing the number of times that blood has been drawn from the blood source in a period of time.

12. The method of claim 11, wherein said assessing the number of times that blood has been drawn from the blood source includes assessing the average number of times that blood has been drawn from the blood source in the period of time.

13. The method of claim 10, wherein said assessing the number of times that blood has been drawn from the blood source includes determining the type of a previous blood draw procedure implemented for the blood source during which blood was drawn from the blood source.

14. The method of claim 13, wherein said determining the type of the previous blood draw procedure includes selecting from a plurality of types of blood draw procedures and giving different values or weights to at least two different types of blood draw procedures when determining whether the blood source is qualified for the first version of the blood separation procedure or the second version of the blood separation procedure and/or determining whether a blood source is not qualified for the first version of the blood separation procedure or the second version of the blood separation procedure.

15. The method of claim 14, wherein a first one of said types of blood draw procedures is the blood separation procedure to be implemented for the blood source, a second one of said types of blood draw procedures is not the blood separation procedure to be implemented for the blood source, and a greater value or weight is given to said first type of blood draw procedure than to said second type of blood draw procedure when determining whether the blood source is qualified for the first version of the blood separation procedure or the second version of the blood separation procedure and/or determining whether a blood source is not qualified for the first version of the blood separation procedure or the second version of the blood separation procedure.

16. The method of claim 1, wherein the blood separation procedure includes separating blood from the blood source into cellular blood components and plasma, and conveying at least a portion of the cellular blood components to a recipient.

17. The method of claim 16, wherein the blood source is the recipient.

18. The method of claim 16, wherein a blood cell separation efficiency of the first version of the blood separation procedure is different from a blood cell separation efficiency of the second version of the blood separation procedure.

19. The method of claim 16, further comprising determining a pre-procedure red blood cell volume of the blood source, wherein the blood separation procedure includes separating blood from the blood source in a fluid flow circuit, a volume of red blood cells less than a selected percentage or maximum volume of the pre-procedure red blood cell volume is allowed to be present in the fluid flow circuit at any time when executing the first version of the blood separation procedure, and a volume of red blood cells different from said selected percentage or maximum volume of the pre-procedure red blood cell volume is allowed to be present in the fluid flow circuit at at least one time when executing the second version of the blood separation procedure.

20. The method of claim 16, further comprising determining a total blood volume of the blood source, wherein the blood separation procedure includes separating blood from the blood source in a fluid flow circuit, a volume of blood less than a selected percentage or maximum volume of the total blood volume is allowed to be present in the fluid flow circuit at any time when executing the first version of the blood separation procedure, and a volume of blood different from said selected percentage or maximum volume of the total blood volume is allowed to be present in the fluid flow circuit at at least one time when executing the second version of the blood separation procedure.

21. The method of claim 1, wherein the first version of the blood separation procedure includes separating blood from the blood source in a first blood separation chamber, and the second version of the blood separation procedure includes separating blood from the blood source in a second blood separation chamber having a different volume than the first blood separation chamber.

22. The method of claim 1, wherein the first version of the blood separation procedure includes a first blood draw phase having a duration, a draw rate, and a blood draw volume, and the second version of the blood separation procedure includes a second blood draw phase having a different duration, draw rate, and/or blood draw volume than said first blood draw phase.

23. The method of claim 1, wherein the first version of the blood separation procedure includes a first fluid return phase having a duration, a return rate, and a fluid return volume, and the second version of the blood separation procedure includes a second fluid return phase having a different duration, return rate, and/or fluid return volume than said first fluid return phase.

* * * * *